US011873272B2

(12) United States Patent
Reardan et al.

(10) Patent No.: US 11,873,272 B2
(45) Date of Patent: *Jan. 16, 2024

(54) ANTIMICROBIAL AND ANTIVIRAL SULFUR CONTAINING GLYCEROL MONOESTER DERIVATIVES

(71) Applicant: Niche Biopharmaceuticals LLC, Shorewood, MN (US)

(72) Inventors: Dayton T. Reardan, Shorewood, MN (US); Paul Brennan, Oxfordshire (GB); Patrick Schlievert, Iowa City, IA (US)

(73) Assignee: Niche Biopharmaceuticals LLC, Shorewood, MN (US)

( * ) Notice: Subject to any disclaimer, the term of this patent is extended or adjusted under 35 U.S.C. 154(b) by 4 days.

This patent is subject to a terminal disclaimer.

(21) Appl. No.: 18/162,301

(22) Filed: Jan. 31, 2023

(65) Prior Publication Data

US 2023/0174473 A1 Jun. 8, 2023

Related U.S. Application Data

(63) Continuation of application No. 17/647,232, filed on Jan. 6, 2022, now Pat. No. 11,365,176, which is a continuation of application No. 16/948,453, filed on Sep. 18, 2020, now Pat. No. 11,572,342.

(51) Int. Cl.
C07C 327/36 (2006.01)
A61P 31/04 (2006.01)
C07D 317/24 (2006.01)

(52) U.S. Cl.
CPC ........... *C07C 327/36* (2013.01); *A61P 31/04* (2018.01); *C07D 317/24* (2013.01)

(58) Field of Classification Search
None
See application file for complete search history.

(56) References Cited

U.S. PATENT DOCUMENTS

| | | | |
|---|---|---|---|
| 4,746,515 A | 5/1988 | Cheng et al. | |
| 5,208,257 A | 5/1993 | Kabara | |
| 5,256,405 A | 10/1993 | Chappell et al. | |
| 5,569,461 A | 10/1996 | Andrews | |
| 5,906,814 A | 5/1999 | Epstein | |
| 6,596,763 B1 | 7/2003 | Thormar et al. | |
| 8,420,627 B2 | 4/2013 | Guthery | |
| 8,512,723 B2 | 8/2013 | Scholz et al. | |
| 8,796,332 B2 | 8/2014 | Schlievert et al. | |
| 9,603,824 B2 | 3/2017 | Schlievert et al. | |
| 9,724,295 B2 | 8/2017 | Schlievert | |
| 10,342,776 B2 | 7/2019 | Schlievert et al. | |
| 10,471,036 B2 | 11/2019 | Scholz et al. | |
| 11,365,176 B2 * | 6/2022 | Reardan | C07C 327/36 |
| 11,572,342 B2 * | 2/2023 | Reardan | C07C 327/06 |
| 2006/0029558 A1 | 2/2006 | Schlievert et al. | |
| 2022/0089535 A1 | 3/2022 | Reardan et al. | |
| 2022/0127224 A1 | 4/2022 | Reardan et al. | |

FOREIGN PATENT DOCUMENTS

WO WO-2022061365 A1 3/2022

OTHER PUBLICATIONS

"U.S. Appl. No. 16/948,453, Non Final Office Action dated Jul. 21, 2022", 8 pgs.
"U.S. Appl. No. 16/948,453, Notice of Allowance dated Nov. 7, 2022", 8 pgs.
"U.S. Appl. No. 16/948,453, Response filed Oct. 21, 2022 to Non Final Office Action dated Jul. 21, 2022", 10 pgs.
"U.S. Appl. No. 17/647,232, Corrected Notice of Allowability dated May 6, 2022", 2 pgs.
"U.S. Appl. No. 17/647,232, Non Final Office Action dated Mar. 30, 2022".
"U.S. Appl. No. 17/647,232, Notice of Allowance dated Apr. 19, 2022".
"CAS Registry 1026972-98-8", (2008).
"CAS Registry 1823920-05-3", (2015).
"International Application Serial No. PCT/US2021/071500, International Search Report dated Feb. 18, 2022", 4 pgs.
"International Application Serial No. PCT/US2021/071500, Invitation to Pay Additional Fees dated Dec. 2, 2021", 2 pgs.
"International Application Serial No. PCT/US2021/071500, Written Opinion dated Feb. 18, 2022", 4 pgs.
"Minimum Inhibitory (MIC) and Minimum Bactericidal Concentration (MBC) Evaluations and R&D Tools", [Online]. Retrieved from the Internet: <URL: https://www.qlaboratories.com/minimum-inhibitory-mic-and-minimum-bactericidal-concentration-mbc-evaluations-as-rd-tools/>, (Accessed Jul. 3, 2020), 3 pgs.
"PubChem-CID-3033877, p. 2", (Aug. 8, 2005), 28 pgs.
"PubChem-SID-24896716, p. 2", this is a purchasable chemical, (Mar. 14, 2018), 6 pgs.
"PubChem-SID-370086359, p. 2", this is a purchasable chemical, (May 25, 2018), 5 pgs.
Gronowitz, et al., "CAS Accession No. 1980:549745.".
Matsumoto, et al., "Duration of Absorption-Enhancing Effect of Sodium Octanoate, Sodium Hexanoate or Glyceryl-1-monooctanoate on Rectal Absorption of Gentamicin in Rabbits", J. Pjarmacobio-Dyn, 13, (1990), 591-596.
Schlievert, Patrick, et al., "Decolonization of Human Anterior Nares of *Staphylococcus aureus* with Use of a Glycerol Monolaurate Nonaqueous Gel", mSphere Research Article Clinical Science and Epidemiology, vol. 5 Issue 4, American Society for Microbiology, (Jul./Aug. 2020), 7 pgs.
Schlievert, Patrick, et al., "Effect of Glycerol Monolaurate on Bacterial Growth and Toxin Production", Antimicrobial Agents and Chemotherapy, vol. 36., American Society for Microbiology, (Mar. 1992), 626-631.

(Continued)

*Primary Examiner* — Joseph R Kosack
(74) *Attorney, Agent, or Firm* — Schwegman Lundberg & Woessner, P.A.

(57) ABSTRACT

The disclosure relates generally novel sulfur containing glycerol mono-ester derivatives and methods useful for treating gram positive, gram negative, fungal and envelope viral infections in a patient.

20 Claims, 4 Drawing Sheets

(56) References Cited

OTHER PUBLICATIONS

Schlievert, Patrick, et al., "Glycerol Monolaurate (GML) and a Nonaqueous Five-Percent GML Gel Kill Bacillus and Clostridium Spores", mSphere Research Article Therapeutics and Prevention, vol. 3 Issue 6, American Society for Microbiology, (Nov./Dec. 2018), 9 pgs.

Schlievert, Patrick, et al., "Glycerol Monolaurate Antibacterial Activity in Broth and Biofilm Cultures", PLoS ONE, Broad-Spectrum GML Antibacterial Activity, vol. 7, Issue 7, (Jul. 2012), 1-12.

Schlievert, Patrick, et al., "Glycerol Monolaurate Does Not Alter Rhesus macaque (Macaca mulatta) Vaginal Lactobacilli and Is Safe for Chronic Use", Antimicrobial Agents and Chemotherapy, vol. 52, No. 12, American Society for Microbiology, (Dec. 2008), 4448-4454.

Schlievert, Patrick, et al., "Superantigen Profile of *Staphylococcus aureus* Isolates from Patients with Steroid-Resistant Atopic Dermatitis", CID 2008:46, Infectious Diseases Society of America, (May 15, 2008), 1562-1567.

Thormar, Halldor, et al., "Inactivation of Enveloped Viruses and Killing of Cells by Fatty Acids and Monoglycerides", Antimicrobial Agents and Chemotherapy, vol. 31, No. 1, American Society for Microbiology, (Jan. 1987), 27-31.

Welch, Jennifer, "Glycerol Monolaurate, an Analogue to a Factor Secreted by Lactobacillus, Is Virucidal against Enveloped Viruses, Including HIV-1", Research Article Therapeutics and Prevention, vol. 11 Issue 3, American Society for Microbiology, (May/Jun. 2020), 1-17.

"International Application Serial No. PCT/US2021/071500, International Preliminary Report on Patentability dated Mar. 30, 2023", 6 pgs.

* cited by examiner

| Compound | TSST-1 Inhibition (μg/ml) |
|---|---|
| GML | 16 |
| SGML | 8 |
| S2GML | <4 |

Figure 3

Escherichia coli

| Compound Tested | Minimum Bactericidal Concentration (µg/ml) | Minimum Inhibitory Concentration (µg/ml) |
|---|---|---|
| GML | 500 | 500 |
| SGML (Clear) | 250 | 250 |
| S2GML (Yellow) | 500 | 500 |

ANTIMICROBIAL AND ANTIVIRAL SULFUR CONTAINING GLYCEROL MONOESTER DERIVATIVES

CROSS-REFERENCE TO RELATED APPLICATION

This application is a continuation of U.S. patent application Ser. No. 17/647,232, filed Jan. 6, 2022, which is a continuation of U.S. patent application Ser. No. 16/948,453, filed Sep. 18, 2020, the contents of both of which are incorporated by reference herein in their entirety.

TECHNICAL FIELD

The present teachings relate generally to novel sulfur containing glycerol mono-ester derivatives and methods useful for treating infections.

BACKGROUND

Microbial and viral infections continue to be important problems, including the microbial development of antibiotic resistance. It is therefore crucial that effective new therapeutic and/or prophylactic antimicrobial agents that are both inexpensive and logistically simple to deliver to appropriate subjects continue to be developed.

Glycerol monolaureate (GML) has been shown extensively to have antimicrobial activity against a plethora of organisms (see for example in Table 1 within Schlievert and Peterson in PLoS ONE; July 2012, 7, e40350) excerpted below.

TABLE 1

Spectrum of antibacterial activity of GML (From Schlievert 2012).

| Bacterium | Gram or Other Stain | Oxygen Tolerance | Strains Tested | Average Bactericidal Concentration (mg/ml) |
|---|---|---|---|---|
| Staphylococcus aureus | Positive | Aerobe | 54 | 300 |
| Streptococcus pyogenes | Positive | Aerotolerant Anaerobe | 4 | 30 |
| Streptococcus agalactiae | Positive | Aerotolerant Anaerobe | 3 | 30 |
| Group C Streptococcus | Positive | Aerotolerant Anaerobe | 1 | 30 |
| Group F Streptococcus | Positive | Aerotolerant Anaerobe | 1 | 20 |
| Group G Streptococcus | Positive | Aerotolerant Anaerobe | 1 | 50 |
| Streptococcus suis | Positive | Aerotolerant Anaerobe | 1 | 50 |
| Streptococcus sanguinis | Positive | Aerotolerant Anaerobe | 1 | 50 |
| Streptococcus pneumoniae Serotype III | Positive | Aerotolerant Anaerobe | 2 | 10 |
| Enterococcus faecalis | Positive | Aerotolerant Anaerobe | 1 | 100 |
| Listeria monocytogenes | Positive | Aerobe | 1 | 50 |
| Bacillus anthracis Sterne | Positive | Aerobe | 1 | 50 |
| Bacillus cereus | Positive | Aerobe | 1 | 50 |
| Peptostreptococcus species | Positive | Anaerobe | 1 | 1 |
| Clostridium perfringens | Positive | Anaerobe | 1 | 1 |
| Neisseria gonorrhoeae | Negative | Aerobe | 1 | 20 |
| Haemophilus influenza Non-typable | Negative | Aerobe | 2 | 50 |
| Gardnerella vaginalis | Negative | Aerobe | 2 | 10 |
| Campylobacter jejuni | Negative | Aerobe | 1 | 1 |

TABLE 1-continued

Spectrum of antibacterial activity of GML (From Schlievert 2012).

| Bacterium | Gram or Other Stain | Oxygen Tolerance | Strains Tested | Average Bactericidal Concentration (mg/ml) |
|---|---|---|---|---|
| Bordetella bronchiseptica | Negative | Aerobe | 1 | 1 |
| Pseudomonas aeruginosa | Negative | Aerobe | 1 | Not Susceptible |
| Burkholderia cenocepacia | Negative | Aerobe | 1 | 500 |
| Pasteurella multocida | Negative | Aerobe | 1 | 500 |
| Prevotella melaninogenica | Negative | Anaerobe | 1 | 50 |
| Bacteroides fragilis | Negative | Anaerobe | 2 | 50 |
| Fusobacterium species | Negative | Anaerobe | 1 | 50 |
| Escherichia coli | Negative | Aerobe | 2 | Not Susceptible |
| Salmonella Minnesota | Negative | Aerobe | 1 | Not Susceptible |
| Enterobacter aerogenes | Negative | Aerobe | 1 | Not Susceptible |
| Proteus vulgaris | Negative | Aerobe | 1 | Not Susceptible |
| Shigella sonnei | Negative | Aerobe | 1 | Not Susceptible |
| Klebsiella pneumoniae | Negative | Aerobe | 1 | Not Susceptible |
| Mycobacterium phlei | Acid Fast | Aerobe | 1 | 100 |
| Mycobacterium tuberculosis | Acid Fast | Aerobe | 1 | 100 |
| Mycoplasma hominis | Cell Wall deficient | Aerobe | 1 | 1 |

While GML can treat clostridium difficile and Bacillus (Schlievert et al., MSphere November/December 2018 Volume 3 Issue 6 e00597-18), as well as kill all envelope virus (Patrick M. Schlievert et al.; ANTIMICROBIAL AGENTS AND CHEMOTHERAPY, Dec. 2008, p. 4448-4454), a more recent paper (Welch, Jennifer L. et al; mBio: 2020 May 5;11(3):e00686-20.) reports that GML is not effective against *Escherichia coli* (*E. coli*).

Drug-resistant infections are the cause of hundreds of thousands of deaths every year. There exists a need for new antibiotics that are able to kill drug-resistant bacteria.

SUMMARY

The instant disclosure relates to compounds of Formula (I),

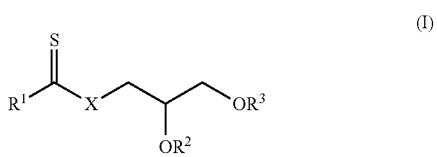

wherein:
R$^1$ is selected from the group consisting of alkyl, alkenyl, and alkynyl;
R$^2$ and R$^3$ are independently selected from the group consisting of hydrogen, COR$^4$, —CON(H)R$^4$, —CO$_2$R$^4$, or P(O)(OR$^4$)$_2$; or, taken together with the carbon to which they are attached, R$^2$ and R$^3$ may form a 3- to 5-membered aliphatic carbocyclic ring;
R$^4$ is H, alkyl, alkenyl, aryl, cycloalkyl, heterocyclyl, or heteroaryl; and X is O or S. or a pharmaceutically acceptable salt thereof.

The disclosure also provides pharmaceutical compositions comprising one or more compounds of formula (I) and an acceptable pharmaceutical carrier.

This disclosure further provides a method of treating an infection in a subject suffering therefrom, comprising administering to the subject suffering therefrom a compound of formula (I).

These and other features, aspects and advantages of the present disclosure will become better understood with reference to the following figures, associated descriptions, and claims.

BRIEF DESCRIPTION OF THE FIGURES

FIG. 3 is the result test conducted with *E. coli* and GML, SGML, and S2GML.

DETAILED DESCRIPTION

Figures 1A, 1B:
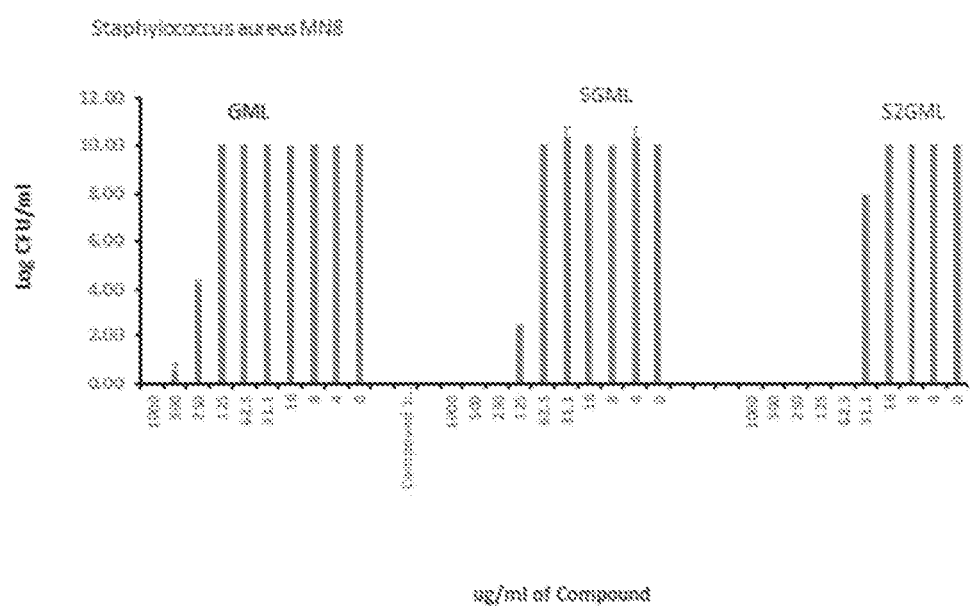
FIGS. 1A-1B are the results of *Staphylococcus aureus* MN8 cultured with various concentrations of GML, SGML, and S2GML

While the concepts of the present disclosure are illustrated and described in detail in the figures and descriptions herein, results in the figures and their description are to be considered as examples and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

The entire contents of each and every patent publication, non-patent publication, and reference text cited herein are hereby incorporated by reference, except that in the event of any inconsistent disclosure or definition from the present specification, the disclosure or definition herein shall be deemed to prevail.

In each of the foregoing and each of the following embodiments, it is to be understood that the formulae include and represent not only all pharmaceutically acceptable salts of the conjugate formulae, but it is appreciated that certain functional groups, such as the hydroxy and like groups form complexes and/or coordination conjugates with water and/or various solvents, in the various physical forms of the compound of formula (I). It is understood that the formulae depicted throughout the disclosure are include and represent hydrates and/or solvates of compounds of formula (I). It is also to be understood that the non-hydrates and/or non-solvates of compounds of formula (I) are described by such formula, as well as the hydrates and/or solvates of the compounds of formula (I).

Definitions

For convenience, before further description of the present disclosure, some terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present disclosure to be more readily understood, some terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Various compounds contained in compositions of the present disclosure may exist in particular geometric or stereoisomeric forms. In addition, polymers of the present disclosure may also be optically active. The present disclosure contemplates all such compounds, including cis-and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this disclosure.

The term "prodrug" as used herein encompasses compounds that, under physiological conditions, are converted into therapeutically active agents. A common method for making a prodrug is to include selected moieties that are hydrolyzed under physiological conditions to reveal the desired molecule. The prodrug can be converted by an enzymatic activity of the host animal. In other words, "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains an alcohol functional group, a prodrug can be formed by the replacement of the hydrogen atom of the hydroxy group with a desired group. For example: an ester, an oxygenated ester, an oxaester, pegylated ester, a hydroxylated ester, an alkyl ester, an amino ester, an alkylamino ester, a dialkylamino ester, a trialkylammonium ester, a carbonate, an alkyl carbonate, an amino carbonate, an alkylamino carbonate, a dialkylamino carbonate, a trialkylammonium carbonate, a carbamate, an alkyl carbamate, an amino carbamate, an alkylamino carbamate, a dialkylamino carbamate, a trialkylammonium carbamate, a substituted phosphate ester, an unsubstituted phosphate ester, an unsubstituted diphosphate ester, a substituted diphosphate ester, an unsubstituted triphosphate ester, a substituted triphosphate ester, a phosphonate ester, a substituted sulfate esters, an unsubstituted sulfate esters, a sulphonate ester, an alpha-acyloxyalkyl, an alpha-phosphoryloxyalkyl, or an alpha-sulphonyloxyalky.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Pharmaceutical compositions of the present disclosure can be non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present disclosure may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the patient of one or more compound of the disclosure. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" or 'subject" refers to a mammal in need of a particular treatment. A patient or subject can be a primate, canine, feline, bovine, or equine. A patient or subject can be a bird. The bird can be a domesticated bird, such as chicken. The bird can be a fowl. A patient or subject can be a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. A straight chain or branched chain alkyl can have 30 or fewer carbon atoms in its backbone (e.g., $C_1$-$C_{30}$ for straight chains, $C_3$-$C_{30}$ for branched chains), or 20 or fewer. Alkyl groups may be substituted or unsubstituted.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene-($CH_2$)-, ethylene-($CH_2CH_2$)-, n-propylene-($CH_2CH_2CH_2$)-, isopropylene-($CH_2CH(CH_3)$)-, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Cycloalkyls can have from 3-10 carbon atoms in their ring structure, or 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, or from one to six carbons, or one to four carbons atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. A substituent designated herein as alkyl can be a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. The "alkylthio" moiety can be represented by one of -(S)-alkyl, -(S)-alkenyl, -(S)-alkynyl, and -(S)-$(CH_2)_m$-$R_{10}$, wherein m and $R_{10}$ are defined below. Representative alkylthio groups include methylthio, ethylthio, and the like. The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O-$(CH_2)_m$-$R_{10}$, where m and $R_{10}$ are described below.

The terms "amine" and "amino" are art-recognized and refer to both unsubstituted and substituted amines, e.g., a moiety that can be represented by the formulae:

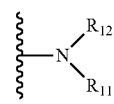

wherein $R_{11}$ and $R_{12}$ each independently represent a hydrogen, an alkyl, an alkenyl, -$(CH_2)_m$-$R_{10}$, or $R_{11}$ and $R_{12}$ taken together with the N atom to which they are attached complete a heterocycle having from 4 to 8 atoms in the ring structure; $R_{10}$ represents an alkenyl, aryl, cycloalkyl, a cycloalkenyl, a heterocyclyl, or a polycyclyl; and m is zero or an integer in the range of 1 to 8. In various embodiments, only one of $R_{11}$ or $R_{12}$ can be a carbonyl, e.g., $R_{11}$, $R_{12}$, and the nitrogen together do not form an imide. In various embodiments, $R_{11}$ and $R_{12}$ each independently represent a hydrogen, an alkyl, an alkenyl, or -$(CH_2)_m$-$R_{10}$. Thus, the term "alkylamine" as used herein means an amine group, as defined above, having a substituted or unsubstituted alkyl attached thereto, i.e., at least one of $R_{11}$ and $R_{12}$ is an alkyl group. An amino group or an alkylamine can be basic, meaning it has a conjugate acid with a $pK_a>7.00$, i.e., the protonated forms of these functional groups have $pK_a$s relative to water above about 7.00.

The term "amide", as used herein, refers to a group

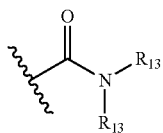

wherein each $R_{13}$ independently represent a hydrogen or hydrocarbyl group, or two $R_{13}$ are taken together with the N atom to which they are attached complete a heterocycle having from 4 to 8 atoms in the ring structure.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Aryl groups can include 5- to 12-membered rings, or 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, 5- to 12-membered rings, or 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic. Each instance of an aryl group may be independently optionally substituted, i.e., unsubstituted (an "unsubstituted aryl") or substituted (a "substituted aryl") with one or more substituents; e.g., for instance from 1 to 5 substituents, 1 to 4 substituents, 1 to 3 substituents, 1 to 2 substituents or just 1 substituent. The aromatic ring may be substituted at one or more ring positions with one or more substituents, such as halogen, azide, alkyl, aryl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. For example, the aryl group can be an unsubstituted $C_5$—$C_{12}$ aryl or can be a substituted $C_5$—$C_{10}$ aryl.

The term "halo", "halide", or "halogen" as used herein means halogen and includes, for example, and without being limited thereto, fluoro, chloro, bromo, iodo and the like, in both radioactive and non-radioactive forms. Halo can be selected from the group consisting of fluoro, chloro and bromo.

The terms "heterocyclyl" or "heterocyclic group" refer to 3- to 12-membered ring structures, 5- to 12-membered rings, or 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aryl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

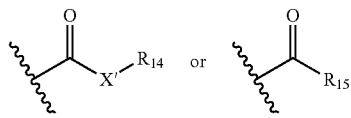

wherein X' is a bond or represents an oxygen, a nitrogen, or a sulfur, and $R_{14}$ represents a hydrogen, an alkyl, an alkenyl, -$(CH_2)_m$-$R_{10}$ or a pharmaceutically acceptable salt, $R_{15}$ represents a hydrogen, an alkyl, an alkenyl or -$(CH_2)_m$-$R_{10}$, where m and $R_{10}$ are as defined above. Where X' is an oxygen and $R_{14}$ or $R_{15}$ is not hydrogen, the formula represents an "ester." Where X' is an oxygen, and $R_{14}$ is as defined above, the moiety is referred to herein as a carboxyl group, and particularly when $R_{14}$ is a hydrogen, the formula represents a "carboxylic acid". Where X' is an oxygen, and $R_{15}$ is a hydrogen, the formula represents a "formate." In general, where the oxygen atom of the above formula is replaced by a sulfur, the formula represents a "thiocarbonyl" group. Where X' is a sulfur and $R_{14}$ or $R_{15}$ is not hydrogen, the formula represents a "thioester" group. Where X' is a sulfur and $R_{14}$ is a hydrogen, the formula represents a "thiocarboxylic acid" group. Where X' is a sulfur and $R_{15}$ is a hydrogen, the formula represents a "thioformate" group. On the other hand, where X' is a bond, and $R_{14}$ is not hydrogen, the above formula represents a "ketone" group. Where X' is a bond, and $R_{14}$ is a hydrogen, the above formula represents an "aldehyde" group.

As used herein, the term "nitro" means —$NO_2$; the term "halogen" designates —F, —Cl, —Br, or —I; the term "sulfhydryl" means —SH; the term "hydroxyl" means —OH; the term "sulfonyl" means —$SO_2$—; the term "azido" means —$N_3$; the term "cyano" means —CN; the term "isocyanato" means —NCO; the term "thiocyanato" means —SCN; the term "isothiocyanato" means —NCS; and the term "cyanato" means —OCN.

As used herein, the definition of each expression, e.g., alkyl, m, n, etc., when it occurs more than once in any structure, is intended to be independent of its definition elsewhere in the same structure.

The term "substituted" refers to moieties having substituents replacing a hydrogen on one or more carbons of the backbone of the moiety. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aryl, or an aromatic or heteroaromatic moiety. The substituents on substituted alkyls can be selected from $C_{1-6}$ alkyl, $C_{3-6}$ cycloalkyl, halogen, carbonyl, cyano, or hydroxyl. The substituents on substituted alkyls can be selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"GML" refers to glycerol monolaureate.

"SGML" refers to glycerol thionomonolaureate (compound 2).

"S2GML" refers to glycerol dithionomonolaureate (compound 1), a dithioester.

For purposes of this disclosure, the chemical elements are identified in accordance with the Periodic Table of the Elements, CAS version, Handbook of Chemistry and Physics, 67th Ed., 1986-87, inside cover.

Compounds of the Disclosure

The disclosure provides compounds of Formula (I):

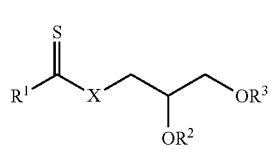

(I)

wherein:
$R^1$ is selected from the group consisting of alkyl, alkenyl, and alkynyl;
$R^2$ and $R^3$ are independently selected from the group consisting of hydrogen, $COR^4$, —$CON(H)R^4$, —$CO_2R^4$, or $P(O)(OR^4)_2$;
or, taken together with the carbon to which they are attached, $R^2$ and $R^3$ may form a 3- to 5-membered aliphatic carbocyclic ring;

$R^4$ is H, alkyl, alkenyl, aryl, cycloalkyl, heterocyclyl, or heteroaryl;
and
X is O or S;
or a pharmaceutically acceptable salt thereof.

$R^1$ can be an alkyl. $R^1$ can be a branched or unbranched (straight) alkyl. $R^1$ can be a $(C_8-C_{20})$alkyl. $R^1$ can be a substituted $(C_8-C_{20})$alkyl. $R^1$ can be an unsubstituted $(C_{10}-C_{16})$alkyl. $R^1$ can be a substituted $(C_{10}-C_{16})$alkyl. $R^1$ can be an unsubstituted $C_{11}$ alkyl. $R^1$ can be an unsubstituted straight chain $C_{11}$ alkyl. $R^1$ can be a substituted $C_{11}$ alkyl. $R^1$ can be an unsubstituted $(C_{10}-C_{16})$alkenyl. $R^1$ can be a substituted $(C_{10}-C_{16})$alkenyl. $R^1$ can be an unsubstituted $C_{11}$ alkenyl. $R^1$ can be a substituted $C_{11}$ alkenyl. $R^1$ can be unsubstituted $(C_{10}-C_{16})$alkynyl. $R^1$ can be a substituted $(C_{10}-C_{16})$alkynyl. $R^1$ can be an unsubstituted $C_{11}$ alkynyl. $R^1$ can be a substituted $C_{11}$ alkynyl.

$R^2$ can be hydrogen. $R^2$ can be $(C_1-C_4)$alkyl. $R^2$ can be —$COR^4$. $R^2$ can be —$CON(H)R^4$. $R^2$ can be —$CO_2R^4$. $R^2$ can be $P(O)(OR^4)_2$. $R^2$ can be $P(P)(OH)_2$.

$R^3$ can be hydrogen. $R^3$ can be $(C_1-C_4)$alkyl. $R^3$ can be —$COR^4$. $R^3$ can be —$CON(H)R^4$. $R^3$ can be —$CO_2R^4$. $R^3$ can he $P(O)(OR^4)_2$. $R^3$ can be $P(O)(OH)_2$.

$R^2$ and $R^3$ can be the same. $R^2$ and $R^3$ can be different. $R^2$ and $R^3$ can be both be hydrogen.

$R^2$ and $R^3$ taken together with the carbon to which they are attached, can form a 3- to 5-membered aliphatic carbocyclic ring $R^4$ can be H. $R^4$ can be alkyl. $R^4$ can be methyl. $R^4$ can be ethyl. $R^4$ can be n-propyl. $R^4$ can be i-propyl. $R^4$ can be n-butyl. $R^4$ can be i-butyl. $R^4$ can be t-butyl. $R^4$ can be cycloalkyl. $R^4$ can be heterocyclyl.

X can be O. X can be S.

Where appropriate, $R^1$, $R^2$, $R^3$, and $R^4$ can be substituted with at least one substituent selected from halogen, alkyl, aryl, alkenyl, alkynyl, cycloalkyl, hydroxyl, amino, nitro, sulfhydryl, imino, amido, sulfamoyl, sulfinyl, alkylthio, sulfonyl, ketone, a heterocyclyl, an aromatic or heteroaromatic moiety, —$CHF_2$-$CF_3$, —CN. If $R^1$, $R^2$, $R^3$, or $R^4$ is substituted with two or more substituents, the substituents can be the same or different.

The compound of the invention can be

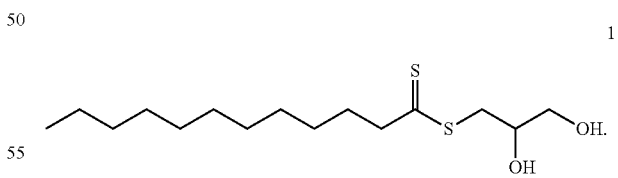

1

The compound of the invention can be

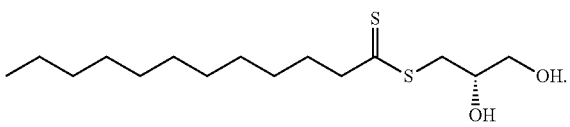 [SMILES: CCCCCCCCCCCC(=S)SC[C@@H](O)CO]

The compound of the invention can be

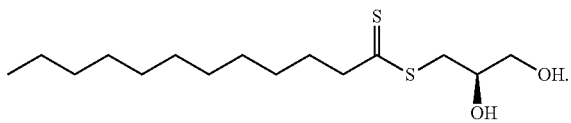 [SMILES: CCCCCCCCCCCC(=S)SC[C@H](O)CO]

The compound of the invention can be

2

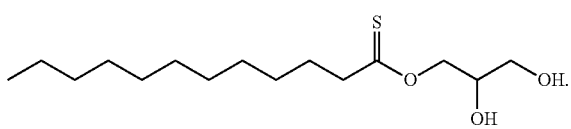

The compound of the invention can be

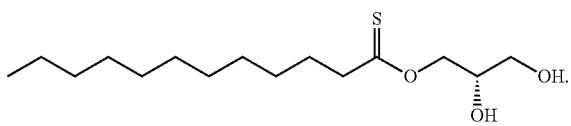 [SMILES: CCCCCCCCCCCC(=S)OC[C@@H](O)CO]

The compound of the invention can be

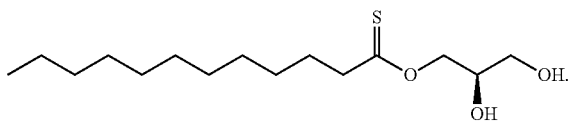

Methods of Treatment

The disclosure relates to a method of treating an infection comprising the step of administering to a subject suffering therefrom a therapeutically effective amount of any one of the aforementioned compounds.

Viral Infections

The disclosure relates to a method of treating a viral infection comprising the step of administering to a subject in need thereof a therapeutically effective amount of any one of the aforementioned compounds.

The viral infection can he a respiratory infection such as infections of the nose, throat, upper airways, and lungs. The infection can be an upper respiratory infection, which include sore throat, sinusitis, and the common cold. Other viral respiratory infections include influenza, pneumonia, and coronaviruses.

The infection can be an inflammation of the upper and lower airways, such as laryngotracheobronchitis or lower airways, such as bronchiolitis.

The viral infection can be an infection of the gastrointestinal tract, such as gastroenteritis, caused by viruses, such as noroviruses and rotaviruses.

The viral infection can be an infection of the liver, which can result in hepatitis.

The viral infection can he an infection of the nervous system. Some viruses, such as the rabies virus and the West Nile virus, infect the brain, causing encephalitis. Others infect the layers of tissue that cover the brain and spinal cord (meninges), causing meningitis or polio.

The viral infection can be an infection of the skin. Viral infections that affect only the skin sometimes result in warts or other blemishes. Many viruses that affect other parts of the body, such as chickenpox, also cause a rash.

The viral infection can be an infection of Placenta and fetus. Some viruses, such as the Zika virus, the rubella virus, and cytomegalovirus, can infect the placenta and fetus in pregnant women.

The viral infection can be an infection caused by an enveloped virus, such as SARS-CoV-2 or influenza, large non-enveloped, virus, or small non-enveloped virus.

Fungal Infections

The disclosure relates to a method of treating a fungal infection comprising the step of administering to a subject in need thereof a therapeutically effective amount of any one of the aforementioned compounds.

The fungal infection can be a nail infection. The fungal infection can be ringworm. The fungal infection can be a yeast infection, such as vaginal candidiasis. The fungal infection can be a candida infection of the mouth, throat, or esophagus.

The fungal infection can be a fungal disease that affect people who live in or travel to certain areas, such as blastomycosis, coccidioidomycosis (Valley fever), cryptococcus gattii infection, hispoplasmosis, or paracoccidioidomycosis.

The fungal infection can be a fungal infection that affect people with weakened immune systems, such as aspergillosis, candidiasis, candida auris infection, cryptococcus neoformans infection, invasive candidiasis, mycormycosis, pneumocystis pneumonia (PCP), or talaromycosis.

The fungal infection can be a fungal eye infection. The fungal infection can be mycetoma. The fungal infection can be sporotrichosis.

Bacterial Infections

The disclosure relates to a method of treating a bacterial infection comprising the step of administering to a subject in need thereof a therapeutically effective amount of any one of the aforementioned compounds.

The bacterial infection can be a skin infection involving only the skin or also involving the soft tissues under the skin. Skin infections include: carbuncles, ecthyma, erythrasma, folliculitis, furuncles, impetigo, lymphadenitis, and small skin abscesses (pus-filled pockets in the skin). Other bacterial skin and skin structure infections include cellulitis, erysipelas, large skin abscesses, lymphangitis, necrotizing skin infections, staphylococcal scalded skin syndrome, and wound infections.

The bacterial infection can be an ear infections or a throat infection, such as strep throat.

Urinary Tract Infections (UTIs)

The infection can be a UTIs. The UTI can be a lower UTs, such as an infections of the bladder (cystitis). The lower UTI can also be an infection of the urethra (urethritis) or prostate (prostatitis)

The UTI can be an upper UTI such as an infections of the kidneys (pyelonephritis).

The UTI can be a bacterial infection, such as a bacterial infection of the lower urinary tract.

The UTI can be a viral infection, such as an infection caused by the herpes simplex virus The UTI can be a fungal, or yeast, infection. The UTI can be vaginitis or candidiasis.

The UTI can he caused by parasites. The UTI can be trichomoniasis, schistosomiasis, or filariasis.

Pharmaceutical Compositions, Routes of Administration, and Dosing

In certain embodiments, the disclosure is directed to a pharmaceutical composition, comprising a compound of the disclosure and a pharmaceutically acceptable carrier. In certain embodiments, the pharmaceutical composition comprises a plurality of compounds of the disclosure and a pharmaceutically acceptable carrier.

In certain embodiments, a pharmaceutical composition of the disclosure further comprises at least one additional pharmaceutically active agent other than a compound of the disclosure. The at least one additional pharmaceutically active agent can be an agent useful in the treatment of infections.

Pharmaceutical compositions of the disclosure can he prepared by combining one or more compounds of the disclosure with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the disclosure being administered, the size of the subject, or the severity of the disease or condition. One of ordinary skill in the art can empirically determine the effective amount of a particular compound of the disclosure and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of a compound are, for human subjects, from about 0.01 milligrams/kg per day to 1000 milligrams/kg per day. Oral doses in the range of 0.5 to 50 milligrams/kg, in one or more administrations per day, can yield therapeutic results. Dosage may be adjusted appropriately to achieve desired drug levels, local or systemic, depending upon the mode of administration. For example, intravenous administration may vary from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related. active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

For clinical use, any compound of the disclosure can be administered in an amount equal or equivalent to 0.2-2000 milligram (mg) of compound per kilogram (kg) of body weight of the subject per day. The compounds of the disclosure can be administered in a dose equal or equivalent to 2-2000 mg of compound per kg body weight of the subject per day. The compounds of the disclosure can be administered in a dose equal or equivalent to 20-2000 mg of compound per kg body weight of the subject per day. The compounds of the disclosure can be administered in a dose equal or equivalent to 50-2000 mg of compound per kg body weight of the subject per day. The compounds of the disclosure can be administered in a dose equal or equivalent to 100-2000 mg of compound per kg body weight of the subject per day. The compounds of the disclosure can be administered in a dose equal or equivalent to 200-2000 mg of compound per kg body weight of the subject per day. Where a precursor or prodrug of the compounds of the disclosure is to be administered rather than the compound itself, it is administered in an amount that is equivalent to, i.e., sufficient to deliver, the above-stated amounts of the compounds of the invention.

The formulations of the compounds of the disclosure can be administered to human subjects in therapeutically effective amounts, e.g., in one or more unit dosage forms as described below. Typical dose ranges are from about 0.01 microgram/kg to about 2 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments may be used to optimize the dose and dosing frequency for any particular compound.

The compounds of the disclosure can be administered at a concentration in the range from about 0.001 microgram/kg to greater than about 500 mg/kg. For example, the concentration may be 0.001 microgram/kg, 0.01 microgram/kg, 0.05 microgram/kg, 0.1 microgram/kg, 0.5 microgram/kg, 1.0 microgram/kg, 10.0 microgram/kg, 50.0 microgram/kg, 100.0 microgram/kg, 500 microgram/kg, 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed by the present invention.

The compounds of the disclosure can be administered at a dosage in the range from about 0.2 milligram/kg/day to greater than about 100 mg/kg/day. For example, the dosage may be 0.2 mg/kg/day to 100 mg/kg/day, 0.2 mg/kg/day, to 50 mg/kg/day, 0.2 mg/kg/day to 25 mg/kg/day, 0.2 mg/kg/day to 10 mg/kg/day, 0.2 mg/kg/day to 7.5 mg/kg/day, 0.2 mg/kg/day to 5 mg/kg/day, 0.25 mg/kg/day to 100 mg/kg/day, 0.25 mg/kg/day to 50 mg/kg/day, 0.25 mg/kg/day to 25 mg/kg/day, 0.25 mg/kg/day to 10 mg/kg/day, 0.25 mg/kg/day to 7.5 mg/kg/day, 0.25 mg/kg/day to 5 mg/kg/day, 0.5 mg/kg/day to 50 mg/kg/day, 0.5 mg/kg/day to 25 mg/kg/day, 0.5 mg/kg/day to 20 mg/kg/day, 0.5 mg/kg/day to 15 mg/kg/day, 0.5 mg/kg/day to 10 mg/kg/day, 0.5 mg/kg/day to 7.5 mg/kg/day, 0.5 mg/kg/day to 5 mg/kg/day, 0.75 mg/kg/day to 50 mg/kg/day, 0.75 mg/kg/day to 25 mg/kg/day, 0.75 mg/kg/day to 20 mg/kg/day, 0.75 mg/kg/day to 15 mg/kg/day, 0.75 mg/kg/day to 10 mg/kg/day, 0.75 mg/kg/day to 7.5 mg/kg/day, 0.75 mg/kg/day to 5 mg/kg/day, 1.0 mg/kg/day to 50 mg/kg/day, 1.0 mg/kg/day to 25 mg/kg/day, 1.0 mg/kg/day to 20 mg/kg/day, 1.0 mg/kg/day to 15 mg/kg/day, 1.0 mg/kg/day to 10 mg/kg/day, 1.0 mg/kg/day. to 7.5 mg/kg/day, 1.0 mg/kg/day to 5 mg/kg/day, 2 mg/kg/day to 50 mg/kg/day, 2 mg/kg/day to 25 mg/kg/day, 2 mg/kg/day to 20 mg/kg/day, 2 mg/kg/day to 115 mg/kg/day, 2 mg/kg/day to 10 mg/kg/day, 2 mg/kg/day to 7.5 mg/kg/day, or 2 mg/kg/day to 5 mg/kg/day.

The compounds of the disclosure can be administered at a dosage in the range from about 0.25 milligram/kg/day to about 25 mg/kg/day. For example, the dosage may be 0.25 mg/kg/day, 0.5 mg/kg/day, 0.75 mg/kg/day, 1.0 mg/kg/day, 1.25 mg/kg/day, 1.5 mg/kg/day, 1.75 mg/kg/day, 2.0 mg/kg/day, 2.25 mg/kg/day, 2.5 mg/kg/day, 2.75 mg/kg/day, 3.0 mg/kg/day, 3.25 mg/kg/day, 3.5 mg/kg/day, 3.75 mg/kg/day. 4.0 mg/kg/day, 4.25 mg/kg/day, 4.5 mg/kg/day, 4.75 mg/kg/day, 5 mg/kg/day, 5.5 mg/kg/day, 6.0 mg/kg/day, 6.5 mg/kg/day, 7.0 mg/kg/day, 7.5 mg/kg/day, 8.0 mg/kg/day, 8.5 mg/kg/day, 9.0 mg/kg/day, 9.5 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 1.8 mg/kg/day, 19 mg/kg/day, 20 mg/kg/day, 21 mg/kg/day, 22 mg/kg/day, 23 mg/kg/day, 24 mg/kg/day, 25 mg/kg/day, 26 mg/kg/day, 27 mg/kg/day, 28 mg/kg/day, 29 mg/kg/day, 30 mg/kg/day, 31 mg/kg/day, 32 mg/kg/day, 33 mg/kg/day, 34 mg/kg/day, 35 mg/kg/day, 36 mg/kg/day, 37 mg/kg/day, 38 mg/kg/day, 39 mg/kg/day, 40 mg/kg/day, 41 mg/kg/day, 42 mg/kg/day, 43 mg/kg/day, 44 mg/kg/day, 45 mg/kg/day, 46 mg/kg/day, 47 mg/kg/day, 48 mg/kg/day, 49 mg/kg/day, or 50 mg/kg/day.

The compound or precursor thereof can be administered in concentrations that range from 0.01 micromolar to greater than or equal to 500 micromolar. For example, the dose may be 0.01 micromolar, 0.02 micromolar, 0.05 micromolar, 0.1 micromolar, 0.15 micromolar, 0.2 micromolar, 0.5 micromolar, 0.7 micromolar, 1.0 micromolar, 3.0 micromolar, 5.0 micromolar, 7.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 60.0 micromolar, 70.0 micromolar, 80.0 micromolar, 90.0 micromolar, 100.0 micromolar, 150.0 micromolar, 200.0 micromolar, 250.0 micromolar, 300.0 micromolar, 350.0 micromolar, 400.0 micromolar, 450.0 micromolar, to greater than about 500.0 micromolar or any incremental value thereof. It is to be understood that all values and ranges between these values and ranges are meant to be encompassed by the present invention.

The compound or precursor thereof can be administered at concentrations that range from 0.10 microgram/mL to 500.0 microgram/mL. For example, the concentration may be 0.10 microgram/mL, 0.50 microgram/mL, 1 microgram/mL, 2.0 microgram/mL, 5.0 microgram/mL, 10.0 microgram/mL, 20 microgram/mL, 25 microgram/mL. 30 microgram/mL, 35 microgram/mL, 40 microgram/mL, 45 microgram/mL, 50 microgram/mL, 60.0 microgram/mL, 70.0 microgram/mL, 80.0 microgram/mL, 90.0 microgram/mL, 100.0 microgram/mL, 150.0 microgram/mL, 200.0 microgram/mL, 250.0 g/mL, 250.0 microgram/mL, 300.0 microgram/mL, 350.0 microgram/mL, 400.0 microgram/mL, 450.0 microgram/mL, to greater than about 500.0 microgram/mL or any incremental value thereof. It is to be understood that all values and ranges between these values and ranges are meant to be encompassed by the present invention.

The formulations of the disclosure can be administered in pharmaceutically acceptable solutions, which may routinely contain pharmaceutically acceptable concentrations of salt, buffering agents, preservatives, compatible carriers, adjuvants, and optionally other therapeutic ingredientsFor use in therapy, an effective amount of the compound can be administered to a subject by any mode that delivers the compound to the desired surface. Administering a pharmaceutical composition may be accomplished by any means known to the skilled artisan. Routes of administration include but are not limited to intravenous, intramuscular, intraperitoneal, intravesical (urinary bladder), oral, subcutaneous, direct injection (for example, into a tumor or abscess), mucosal (e.g., topical to eye), inhalation, and topical.

For intravenous and other parenteral routes of administration, a compound of the disclosure can be formulated as a lyophilized preparation, as a lyophilized preparation of liposome-intercalated or -encapsulated active compound, as a lipid complex in aqueous suspension, or as a salt complex. Lyophilized formulations are generally reconstituted in suitable aqueous solution, e.g., in sterile water or saline, shortly prior to administration.

For oral administration, the compounds can be formulated readily by combining the active compound(s) with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), if desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also contemplated are oral dosage forms of the compounds of the disclosure. The compounds of the disclosure may be chemically modified so that oral delivery of the derivative is efficacious. Generally, the chemical modification contemplated is the attachment of at least one moiety to the compound itself, where said moiety permits (a) inhibition of acid hydrolysis; and (b) uptake into the blood stream from the stomach or intestine. Also desired is the increase in overall stability of the compounds and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., Appl Biochem 4:185-9 (1982). Other polymers that could be used are poly-1,3-dioxolane and poly-1,3,6-tioxocane. For pharmaceutical usage, as indicated above, polyethylene glycol moieties are suitable.

The location of release of a compound of the disclosure may be the stomach, the small intestine (the duodenum, the jejunum, or the ileum), or the large intestine. One skilled in the art has available formulations which will not dissolve in the stomach, yet will release the material in the duodenum or elsewhere in the intestine. The release can avoid the deleterious effects of the stomach environment, either by protection of the compound of the disclosure or by release of the compound beyond the stomach environment, such as in the intestine.

To ensure full gastric resistance a coating impermeable to at least pH 5.0 is essential Examples of the more common inert ingredients that are used as enteric coatings are cellulose acetate trimellitate (CAT), hydroxypropylmethylcellulose phthalate. (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm or smaller (i.e. nanoparticles). The formulation of the material for capsule administration could also be as a powder, lightly , compressed plugs or even as tablets. The therapeutic could be prepared by compression.

Colorants and flavoring agents may all be included. For example, the compound of the disclosure may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium alts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester ; methyl cellulose and carboxymethyl cellulose. These surfactants could be present in the formulation of the compound of the disclosure or derivative either alone or as a mixture in different ratios.

Pharmaceutical preparations which can be used orally in unit dosage form include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, compounds for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds disclosed herein (or salts thereof). The compound is delivered to the lungs of a mammal while inhaling and traverses across the lung epithelial lining to the blood stream. Other reports of inhaled molecules include Adjei et al., Pharm Res 7:565-569 (1990) Adjei et al., Int J Pharmaceutics 63:135-144 (1990) (leuprolide acetate); Braquet et al., Cardiovasc Pharmacol 13(suppl. 5):143-146 (1989) (endothelin-1); Hubbard et al., Annal Int Med. 3:206-212 (1989) (a 1-antitrypsin); Smith et al., 1989, J Clin Invest 84:1145-1146 (a 1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, J Immunol 140:3482-3488 (interferon-gamma and tumor necrosis factor alpha) and Platz et al., U.S. Pat. No. 5,284,656 (granulocyte colony stimulating factor; incorporated by reference). A method and composition for pulmonary delivery of drugs for systemic effect is described in U.S. Pat. No. 5,451,569 (incorporated by reference), issued Sep. 19, 1995 to Wong et al.

Contemplated for use in the practice of this disclosure are a wide range of mechanical devices designed for pulmonary delivery of therapeutic products, including but not limited to nebulizers, metered dose inhalers, and powder inhalers, all of which are familiar to those skilled in the art.

Nasal delivery of a pharmaceutical composition of the present disclosure is also contemplated. Nasal delivery allows the passage of a pharmaceutical composition of the present disclosure to the blood stream directly after administering the therapeutic product to the nose, without the necessity for deposition of the product in the lung. Formulations for nasal delivery include those with dextran or cyclodextran.

The compounds, when it is desirable to deliver them systemically, may be formulated for parenteral administration by injection, e.g.. by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butler or other glycerides.

In addition to the formulations described above, a compound may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R., Science 249:1527-33 (1990).

The compound of the disclosure and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v; parabens (0.01-0.25% w/v) and thimerosal (0.004-0.02% w/v).

Pharmaceutical compositions of the disclosure contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present disclosure, and with each other, in a manner such that there is no interaction which would substantially impair the desired pharmaceutical efficiency.

The therapeutic agent(s), including specifically but not limited to a compound of the disclosure, may be provided in particles. Particles as used herein means nanoparticles or microparticles (or in some instances larger particles) which can consist in whole or in part of the compound of the disclosure or the other therapeutic agent(s) as described herein. The particles may contain the therapeutic agents) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or non biodegradable material or combinations thereof. The particles may be microcapsules which contain the compound of the disclosure in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) Macromolecules 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly (isopropyl acrylate), poly(isobutyl acrylate), and poly(octadecyl acrylate).

The therapeutic agent(s) may he contained in controlled release systems. The term "controlled release" is intended to refer to any thug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that can results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term. sustained release implant may be particularly suitable for treatment of chronic conditions. "Long-term" release, as used herein, means that the implant is constructed and arranged to deliver therapeutic levels of the active ingredient for at least 7 days, and up to 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the disclosure contained herein in view of information known to the ordinarily skilled artisan, and may be made without departing from the scope of the disclosure or any embodiment thereof. Having now described the present disclosure in detail, the same will be more clearly understood by reference to the following examples, which are included herewith for purposes of illustration only and are not intended to be limiting of the disclosure.

EXAMPLES

The invention now being generally described, it will be more readily understood by reference to the following examples, which are included merely for purposes of illustration of certain aspects and embodiments of the present invention and are not intended to limit the invention.

Material and Methods

General Chemical Synthesis

Several methods for the chemical synthesis of the example compounds are described herein. These and/or other well-known methods may be modified and/or adapted in known ways in order to facilitate the synthesis of additional compounds described herein.

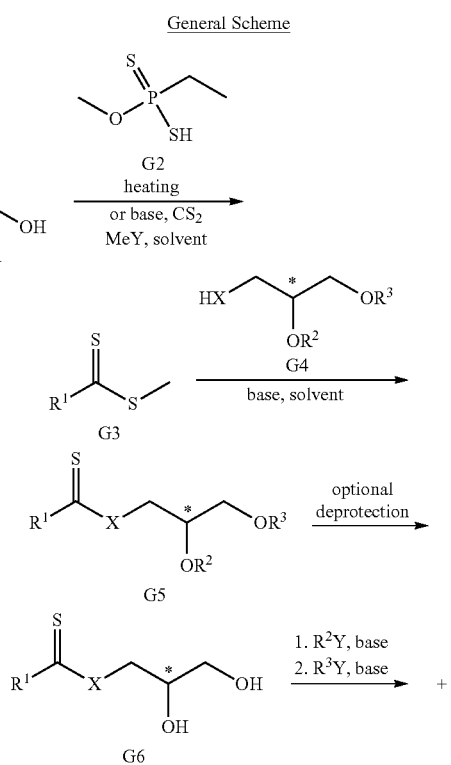

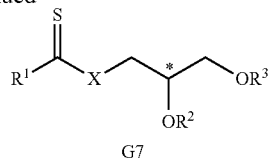

In one approach, certain compounds described herein may conveniently be prepared by reaction of a suitably substituted carboxylic acid G1 with a reagent such as G2 to give an intermediate G3. Other thionation reagents may also be used such as Lawesson's reagent, P4S10, Davy's reagent and other similar compounds followed by methylation. Alternatively, G3 may be prepared by deprotonation of G1 with a strong base such as lithium diisopropylamide, reaction with carbon disulfide and then a methylating reagent MeY, such as iodomethane. The intermediate G3 can be further modified with alcohols or thiols G4 where R2 and R3 are either protecting groups or variable substituents. If R2 and R3 are variable substituents, compound G5 would be a final example. In the case that R2 and R3 are protecting groups, or a single diol protecting group that forms a cyclic diether, deprotection of intermediate G5 will furnish G6, which may be a final example or an intermediate. In the case that R2 and R3 are a cyclic diether protecting group, deprotection can be done conveniently with aqueous acid. There are many other possibilities for R2 and R3 as protecting groups such as ethers, silyl ethers or esters which may be distinct or combined into a single group including both R2 and R3. If an intermediate, G6 can be modified further with R2 and R3 groups to give compounds G7 with suitable reagents R2Y and R3Y where Y is a leaving group such as halogen, carboxyl or sulfonyl group. Intermediate G4 may either be achiral, racemic or a single enantiomer.

saturated $NaHCO_3$ (25 mLX3) and saturated sodium chloride (30 mLX1), dried over $Na_2SO_4$. It was concentrated by evaporation under reduced pressure. The residue was purified by silica column chromatography (Petroleum ether) to give compound 12 (0.57 g, 46%).

$^1$H NMR (300 MHz, $CDCl_3$) δ 3.04 (m, J=7.5 Hz 2H), 2.62 (s, 3H), 1.85-1.78 (m, 2H), 1.37-1.26 (m, 16H), 0.88 (t, J=7.2 Hz, 3H).

O-((2,2-dimethyl-1,3-dioxolan-4-yl)methyl) dodecanethioate (13): (2,2-Dimethyl-1,3-dioxolan-4-yl)methanol (0.45 mL, 3.60 mmol) was dissolved in dichloromethane (11 mL) containing sodium methoxide (0.19 g, 3.60 mmol). Compound 12 (0.59 g, 2.40 mmol) was added and the solution was stirred at room temperature for 0.5 h. It was concentrated by evaporation under reduced pressure. Diethyl ether (60 mL) was added to it and washed with water (15 mL) and saturated sodium chloride (20 mL ×2) and dried over $Na_2SO_4$. It was concentrated by evaporation under reduced pressure. The residue was purified by silica column chromatography (Petroleum ether: Ethyl acetate=90:1-60:1) to give compound 13 (115 mg, 14%) and compound 12 (110 mg).

$^1$H NMR (300 MHz, $CD_3OD$) δ 4.51-4.11 (m, 3H), 4.15-4.10 (m, 1H), 3.82-3.77 (m, 1H), 2.75 (t, J=7.5 Hz, 2H), 1.80-1.70 (m, 2H), 1.41 (s, 3H), 1.35 (s, 3H), 1.30 (m, 16H), 0.90 (t, J=6.9 Hz, 3H).

SGML: To a solution of compound 13 (0.382 g, 1.15 mmol) in tetrahydrofuran (6.5 mL) was added acetic acid aqueous solution (8.18 mL, 60%) under $N_2$. The reaction mixture was heated to 120° C. for 1.5 h. It was cooled to room temperature. Diethyl ether (100 mL) was added to it, was washed water (30 mL ×2) with saturated $NaHCO_3$ (30 mL ×3) and saturated sodium chloride (20 mL ×2) and dried over $MgSO_4$. It was concentrated by evaporation under

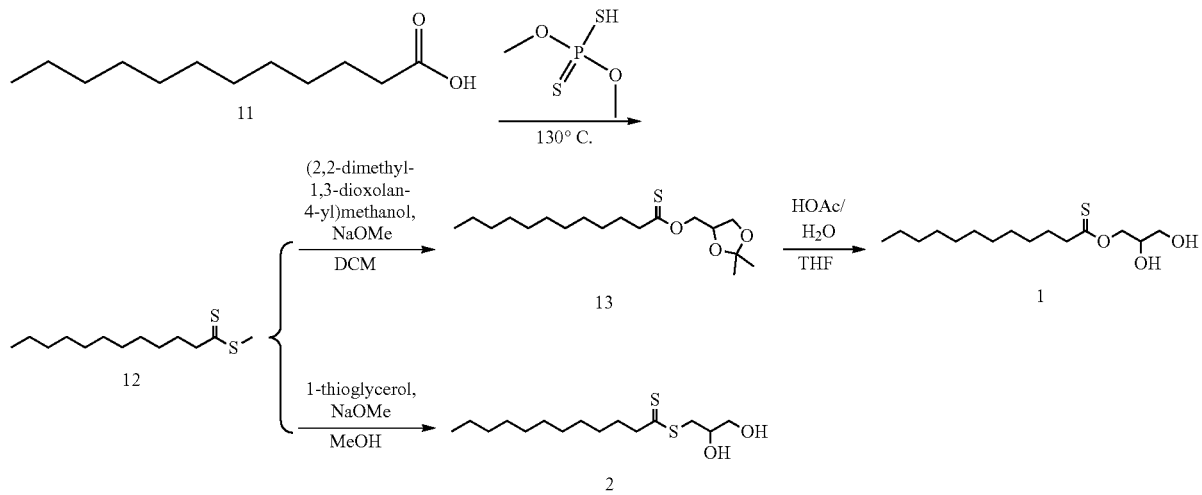

Chemistry Scheme 1

Example 1 (SGML)

Methyl dodecanedithioate (12): Compound 11 (1.00 g, 5 mmol) was added to O,O-dimethyl S-hydrogen phosphorodithioate (5.0 mL) under $N_2$. The reaction mixture was heated to 130° C. for 1.5 h. It was cooled to room temperature. Diethyl ether (50 mL) was added to it, was washed with reduced pressure. The residue was purified by silica column chromatography (Petroleum ether: Ethyl acetate=3:2) to give compound 2 (SGML) (100 mg, 29.8%).

$^1$H NMR (300 MHz, $CD_3OD$) δ 3.83-3.79 (m, 1H), 3.57-3.50 (m, 3H), 3.26 (d, J=7.5 Hz, 1H), 3.03 (t, J=7.2 Hz, 2H), 1.88-1.78 (m, 2H), 1.39-1.29 (m, 16H), 0.90 (t, J=6.6 Hz, 3H).

Example 2 (S2GML)

1-Thioglycerol (0.26 mL, 2.95 mmol; freed of water by azeotropic distillation with toluene was dissolved in absolute methanol (19.4 mL) containing a catalytic amount of sodium methoxide (16 mg, 0.30 mmol). Compound 12 (0.87 g, 3.54 mmol) was added and the solution was stirred at room temperature for 1.5 h. Diethyl ether (100 mL) was added to it and washed with water (20 mL) and saturated sodium chloride (40 mL) and dried over MgSO$_4$. It was concentrated by evaporation under reduced pressure. The residue was purified by silica column chromatography (Petroleum ether: Ethyl acetate=3:2) to give compound 2 (S2GML) (89 mg, 19%).

$^1$H NMR (300 MHz, CD$_3$OD) δ 3.83-3.79 (m, 1H), 3.57-3.50 (m, 3H), 3.26 (d, J=7.5 Hz, 1H), 3.03 (t, J=7.2 Hz, 2H), 1.88-1.78 (m, 2H), 1.39-1.29 (m, 16H), 0.90 (t, J=6.6 Hz, 3H).

ylamine (7.3 mL, 52.2 mmol) in dry CH$_2$Cl$_2$ (50 mL) at 0° C. The flask is kept in a refrigerator for 2 d. After dilution with CH$_2$Cl$_2$ (225 mL), the solution is washed twice with water (45 mL). After evaporation of the solvent, the residue is dissolved in diethyl ether (75 mL) and the organic layer is dried with MgSO$_4$, filtered and concentrated under reduced pressure. The crude tosylate is dissolved in acetone (120 mL) and potassium thioacetate (2.95 g, 25.8 mmol) is added. The resulting solution is refluxed for 24 h. After filtration and concentration, the residue is treated with water (20 mL) and extracted with diethyl ether (2×100 mL). The organic layer is dried with MgSO$_4$, filtered and concentrated to give the thioacetate which is dissolved in EtOH (3 mL) and 5 N NaOH (5.5 mL, 27.7 mmol) is added. The resulting solution is stirred for 9 h at 20° C. The reaction is carefully neutralized with acetic acid and the EtOH is evaporated. After extraction with ether (3×10 mL), the combined organic layers are washed with a saturated solution of NaHCO$_3$,

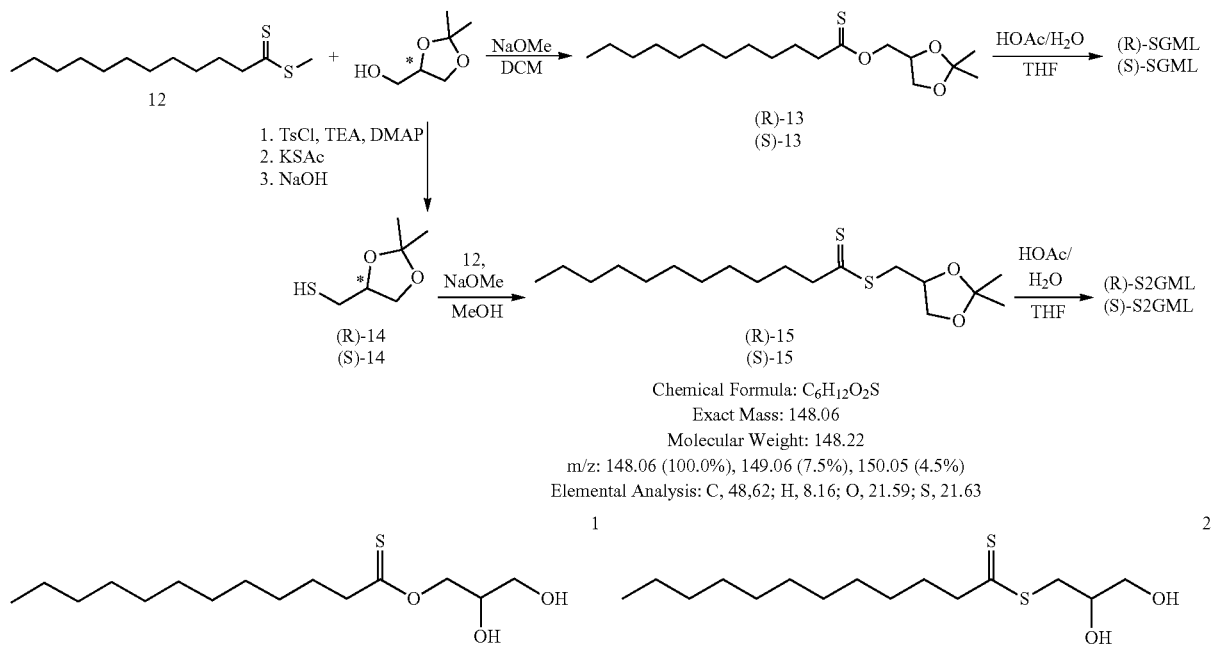

Example 3: ((R)-SGML)

((R)-SGML) is prepared in a method analogous to Example 1 from (S)-(2,2-dimethyl-1,3-dioxolan-4-yl) methanol.

Example 4: ((S)-SGML)

((S)-SGML) is prepared in a method analogous to Example 1 from (R)-(2,2-dimethyl-1,3-dioxolan-4-yl) methanol.

Example 5: ((R)-S2GML)

[(4R)-2,2-Dimethyl-1,3-dioxolan-4-yl]methanethiol ((R)-14): A solution of toluene-p-sulfonyl chloride (5.2 g, 27.2 mmol) in dry CH$_2$Cl$_2$ (30 mL) is added to a solution of (S)-(2,2-dimethyl-1,3-dioxolan-4-yl)methanol (3 g, 22.7 mmol), DMAP (0.01 equiv., 28 mg, 0.23 mmol) and triathdried with MgSO$_4$ and concentrated. The residue is finally purified by flash column chromatography (C$_5$H$_{12}$/Et$_2$O, 24:1) to afford (R)-14.

(R)-(2,2-dimethyl-1,3-dioxolan-4-yl)methyl dodecanedithioate ((R)-15): (R)-14 (0.30 g, 2.0 mmol) was dissolved in absolute methanol (19.4 mL) containing a catalytic amount of sodium methoxide (16 mg, 0.30 mmol). Compound 12 (0.58 g, 2.4 mmol) was added and the solution was stirred at room temperature for 1.5 h. Diethyl ether (100 mL) was added to it and washed with water (20 mL) and saturated sodium chloride (40 mL) and dried over MgSO$_4$. It was concentrated by evaporation under reduced pressure. The residue was purified by silica column chromatography (Petroleum ether: Ethyl acetate=3:2) to give the title compound (140 mg, 20%).

(R)-S2GML: To a solution of compound (R)-15 (0.10 g, 0.29 mmol) in tetrahydrofuran (5 mL) was added acetic acid aqueous solution (5 mL, 60%) under N$_2$. The reaction mixture was heated to 120° C. for 1.5 h. It was cooled to room temperature. Diethyl ether (50 mL) was added to it, was washed water (25 mL ×2) with saturated NaHCO₃ (25 mL ×3) and saturated sodium chloride (20 mL ×2) and dried over MgSO₄. It was concentrated by evaporation under reduced pressure. The residue was purified by silica column chromatography (Petroleum ether: Ethyl acetate=3:2) to give Example 5 ((R)-S2GML) (44 mg, 50%).

¹H NMR (300 MHz, CD₃OD) δ 3.83-3.79 (m, 1H), 3.57-3.50 (m, 3H), 3.26 (d, J=7.5 Hz, 1H), 3.03 (t, J=7.2 Hz, 2H), 1.88 -1.78 (m, 2H), 1.39-1.29 (m, 16H), 0.90 (t, J=6.6 Hz, 3H).

Example 6: ((S)-S2GML)

((S)-S2GML) is prepared in a method analogous to Example 5 from (R)-(2,2-dimethyl-1,3-dioxolan-4-yl)methanol.

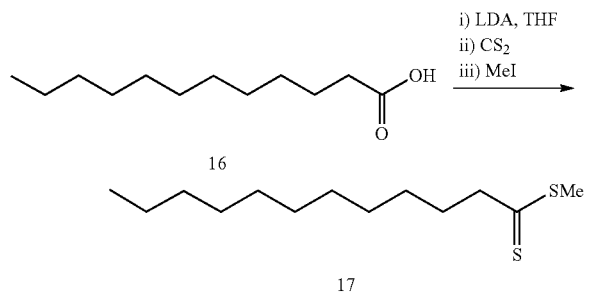

To a solution of dodecanoic acid (30 g, 150 mmol) in anhydrous THF (1000 mL) at 0° C. was added LDA (Lithium diisopropylamide) (2M in THF (tetrahydrofuran), 330 mmol) dropwise with continuous stirring. After complete addition, the reaction was heated to 35° C. for 30 mins, forming a thick brown slurry. The reaction was cooled to −30° C. and CS₂ (12.6 g, 165 mmol) was added dropwise. The reaction was stirred for a further 15 minutes, and cooled to −50° C. MeI (21.3 g, 150 mmol) was added dropwise and the reaction stirred for 30 mins. The reaction was quenched by pouring into ice cold 1M HCl (1000 mL). The aqueous layer was extracted with pentane, the combined organic layers were washed with brine, dried over sodium sulfate and concentrated in vacuo. The crude product was purified by flash column chromatography with pentane as the eluent to give 17 as a yellow oil, (13.4 g, 54.37 mmol, 36%).

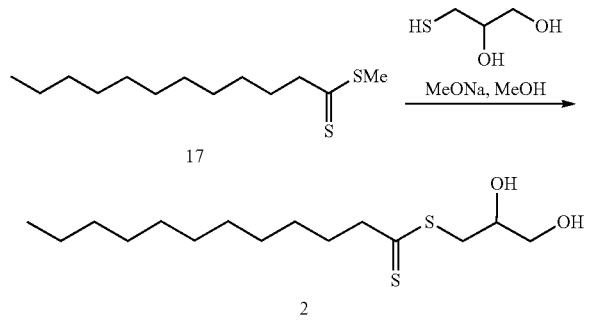

To a solution of 1-thioglycerol (4.02 g, 37.2 mmol) in methanol (450 mL) was added sodium methoxide (402 mg, 7.44 mmol). The reaction stirred for 5 mins, followed by addition of 17 (11 g, 44.6 mmol). The reaction was stirred for 2 h, diluted with water (750 mL) and extracted with ethyl acetate. The combined organic layers were washed with brine, dried over sodium sulfate and concentrated in vacuo. The crude product was purified by FCC (3:2 PE:EA), followed by recrystallisation from cyclohexane to give 2 as a yellow crystalline solid, 1.06 g, 3.46 mmol, 9.3%).

¹H NMR (400 MHz, DMSO-d₆) δ 5.12 (d, J=5.5 Hz, 1H), 4.74 (t, J=5.7 Hz, 1H), 3.73-3.63 (m, 1H), 3.47 (dd, J=13.3, 4.3 Hz, 1H), 3.39 (dt, J=10.8, 5.4 Hz, 1H), 3.17 (dd, J=13.3, 7.9 Hz, 1H), 3.00 (t, J=7.5 Hz, 2H), 1.74 (p, J=7.3 Hz, 2H), 1.24 (s, 16H), 0.85 (t, J=6.7 Hz, 3H).

Example 8

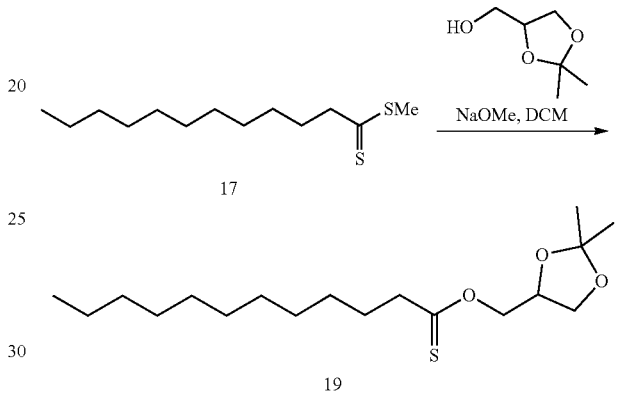

To a solution of (2,2-dimethyl-1,3-dioxolan-4-yl)methanol (7.40 g, 56.0 mmol) in dichloromethane (DCM 500 mL) was added NaOMe (3.03 g, 56.0 mmol) to form a suspension. 17 (9.2 g, 37.3 mmol) was added and the reaction stirred for 1 h. The reaction was diluted with water (500 mL) and extracted with DCM. The combined organic layers were dried over sodium sulfate and concentrated in vacuo. The crude product was purified by FCC (2% EA/PE) to give 19 as a colourless oil (4.4 g, 12.70 mmol, 34%).

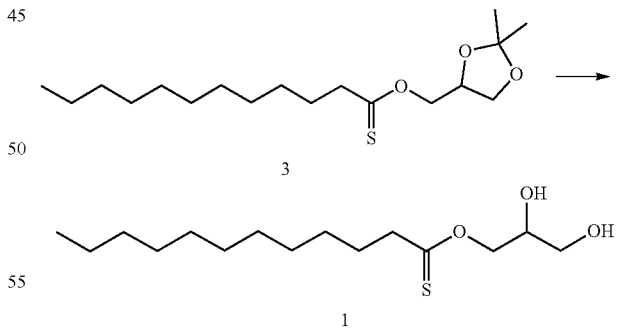

A solution of 19 (4.4 g, 12.70 mmol) in acetic acid (10 mL), THF (5 mL) and water (5 mL) was heated to 90° C. for 30 minutes. The reaction was quenched by pouring carefully into ice NaHCO₃, and extracted with ethyl acetate. The combined organic layers were washed with brine, dried over sodium sulfate and concentrated in vacuo. The crude product was purified by FCC followed by recrystallisation from cyclohexane to give 1 as colourless needles, 740 mg, 2.55 mmol, 20%).

¹H NMR (400 MHz, DMSO-d₆) δ 5.02 (br s, J=5.3 Hz, 1H), 4.71 (br s, 1H), 4.43 (dd, J=11.4, 3.8 Hz, 1H), 4.29 (dd, J=11.4, 6.5 Hz, 1H), 3.83 (br s, J=6.9 Hz, 1H), 3.46-3.38 (m, 2H), 2.72 (t, J=7.5 Hz, 2H), 1.67 (p, J=7.3 Hz, 2H), 1.34-1.18 (m, 16H), 0.86 (t, J=6.8 Hz, 3H).

Antibacterial Activity-Results

The SGML and S2GML compounds have been shown in the examples below to perform at least as well if not much better than the native GML.

Example 9

*Staphylococcus aureus*, including toxic shock syndrome strains, are among the bacteria most resistant to glycerol monolaurate (GML). All strains of *S. aureus* tested remain susceptible to ≤500 μg/ml. For most *S. aureus* strains, GML is bactericidal at 250 μg/ml. When examined, other Gram-positive bacteria and those Gram-negative bacteria with an incomplete lipopolysaccharide (in their case called lipo-oligosaccharide), are killed by GML concentrations of approximately 25-50 μg/ml. Gram-negative bacteria with an intact lipopolysaccharide, such as *Escherichia coli*, are completely resistant to GML unless accelerants are added to increase activity. Such accelerants would include low pH and EDTA addition to remove calcium and magnesium from the lipopolysaccharide layer. Under those conditions, GML is able to kill such Gram-negative bacteria at 25-50 μg/ml.

The reason *S. aureus* strains exhibit a degree of resistance to GML, is that these bacteria produce a glycerol ester hydrolase (lipase) that can degrade GML into lauric acid and glycerol and then use the products as nutrient sources. Our experience is that lipase cannot be produced at GML concentrations about 300 μg/ml.

The following protocol was developed to test GML plus SGML and S2GML, wherein sulfur residues are inserted to replace oxygens in the GML molecule.

Toxic shock syndrome (TSS) *S. aureus* strain MN8, which produces TSS Toxin-1 (TSST-1) was cultured overnight in Difco, Detroit, MI Todd Hewitt broth in a 125 ml Erlenmeyer flask to be sure it reached stationary phase. For this experiment, all cultures were aerobic at 37° C. with 150 RPM gyrotary shaking. Stationary phase with this microbe is 1.0×10¹⁰ colony-forming units (CFUs)/ml.

The next morning the culture was diluted to approximately 5×10⁶/ml in 1 ml amounts of Todd Hewitt broth in 5 ml polystyrene test tubes. The tubes contained serial two-fold dilutions of glycerol monolaurate, SGML, or S2GML. The control tubes contained no GML or SGML and S2GML compounds. The compounds were tested in triplicate. GML and SGML and S2GML were solubilized at 100 mg/ml in absolute ethanol. The control tube contained the highest volume of ethanol that was used to deliver the compounds to each 1 ml test tube.

After 24-hour incubation, serial 10-fold dilution plate counts were performed on each tube with plating onto Todd Hewitt 1.5% agar plates. Once plated, the plates were incubated aerobically for 24 hours at 37° C. Counts were made to determine CFUs/ml.

The CFUs/ml were log-transformed and mean ±SD were determined.

The test tubes from the prior day's 24-hour growth were treated with 4 volumes of absolute ethanol. After 2-hours to precipitate TSST-1, the precipitates were collected by 4000 x g centrifugation for 10 minutes and pouring off the supernates. The precipitates were dried for 30 minutes in a laminar flow hood to dry off ethanol. The precipitates were then diluted to 0.1 ml with water giving a 10× concentration of TSST-1. Serial two-fold dilutions of the TSST-1 were made in distilled water. Twenty microliters of each dilution were set up in a standard double immunodiffusion assay. The center well contained hyperimmune polyclonal antibodies against TSST-1. The diluted toxin preparations were added in a hexagonal pattern around the outside and 4 mm away from the antibodies. The slides were incubated exactly 4 hours at 37° C. and then examined for visible precipitin arcs. The positive control, purified TSST-1 was visible at 6 μg/ml. Thus, the lower limit of TSST-1 detection in the test samples was 0.6 μg/ml, being 10× concentrated.

Each slide was read and TSST-1 μg/ml determined. Because there is a two-fold limit on sensitivity of this assay, there was a mean but no standard deviation. Data were recorded as means only.

Using the standard MIC and MBC assay above with *Staphylococcus aureus* strain MN8, SGML and S2GML were tested with GML.

FIGS. 1A and 1B show the log of the CFU/mL of *Staphylococcus aureus* MN8 cultured with various concentrations of GML, SGML, and S2GML. SGML and S2GML can be distinguished easily by color. SGML is clear in ethanol and S2GML is yellow. The yellow one (S2GML) clearly has more activity, though both are more active than GML. The CFUs were log converted so minor variations in data would not be skewed. All data points below the zero compound added are statistically significant. Normally a 3 log drop is considered bactericidal. There are small standard deviations on the log CFUs/ml.

A second study was conducted where toxic shock syndrome superantigen (TSST-1) was measured.

Figures 2A, 2B:
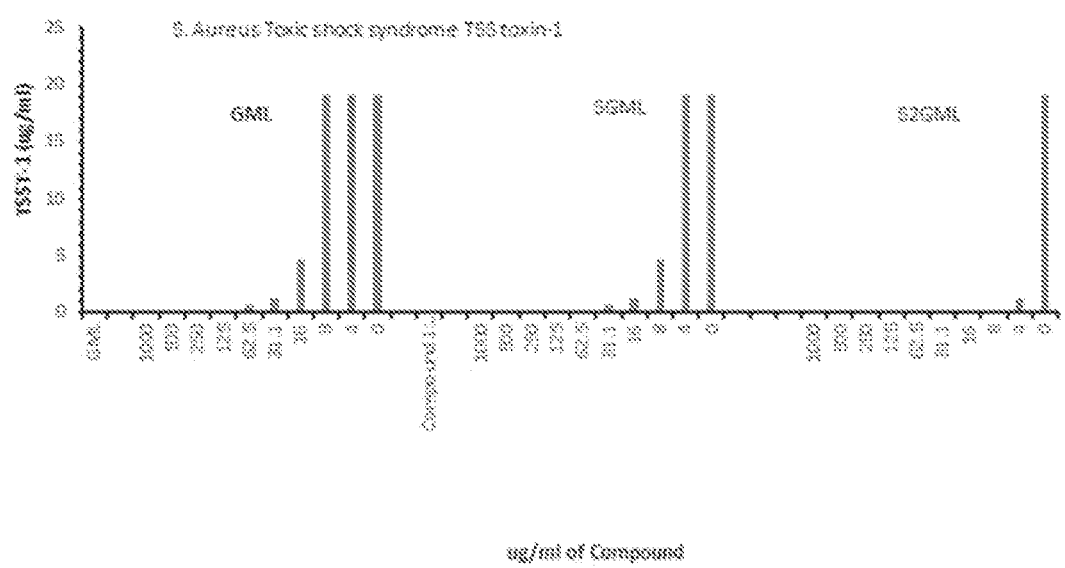
FIGS. 2A-2B are the results of inhibition of TSST-1 by GML, SGML, and S2GML.

FIGS. 2A and 2B show the results of each compound on the reduction in TSST-1. TSST-1 is shut off prior to the impact on growth.

Example 10

The same MIC and MBC test was conducted with *E. coli* and SGML was found to be more effective than GML rather than the S2GML which at least in this assay performed similarly to GML (FIG. 3).

The conditions for this test were the same as in the above example with *S. aureus* MN8. The *E. coli* strain was a laboratory strain from a patient with a confirmed urinary tract infection. The strain is maintained in the laboratory at −80° C.

Both SGML and S2GML have been shown to have greater activity than the parent GML compound in minimum inhibitory concentration (MIC) and minimum bactericidal concentration (MBC) assays against the *Staphylococcus aureus* MN8 strain. Both were more effective than GML which had a MIC of 250 μg/mL and a MBC of 250 μg/mL in the assay. The SGML had a MIC of 125 μg/mL and a MBC of 125 μg/mL and the S2GML was shown to have a MIC of 31.125 μg/mL and a MBC of 63.5 μg/mL. In addition both SGML and S2GML show a greater reduction in the toxin TSST-1 where GML inhibition was found to be at 16 μg/mL and the SGML was at 8 μg/mL and the S2GML inhibition of TSST-1 was <4 μg/mL using the same *Staphylococcus aureus* MN8 strain.

| Escherichia coli | | |
|---|---|---|
| Compound Tested | Mininum Bactericidal Concentration (μg/ml) | Minimum Inhibitory Concentration (μg/ml) |
| GML | 500 | 500 |
| SGML (Clear) | 250 | 250 |
| S2GML (Yellow) | 500 | 500 |

Example 11. Esterase Resistance for the SGML and S2GML Compounds.

Figure 4:
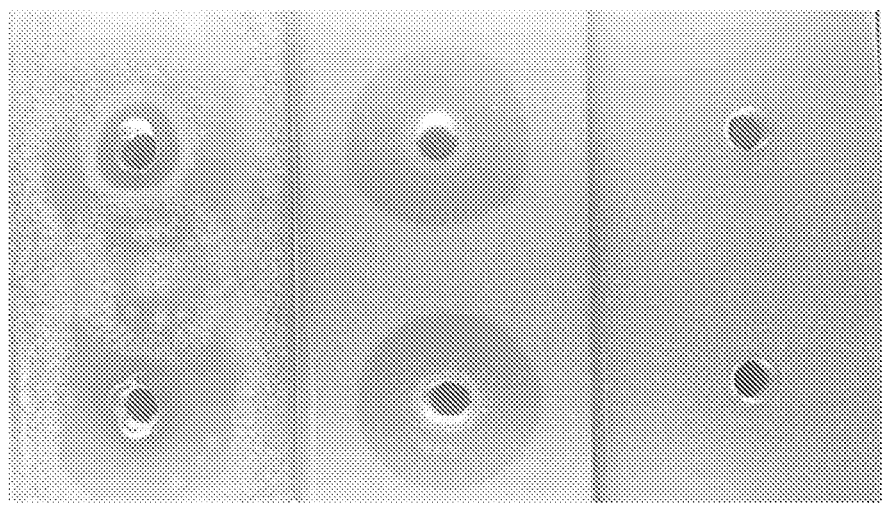
FIG. 4 is the photograph of esterase activity of two *Staphylococcus aureus* strains treated with GML, SGML, and S2GML.

Protocol for Lipase (glycerol ester hydrolase) assay:
1. Two separate samples of lipase at 25 ug/ml were prepared.
2. Microscope slides were made up with 500 ug/ml of GML, SGML, or S2ML compounds. These slides contained 0.85% agarose (Difco) heat solubilized into PBS (0.005M $NaPO_4$ pH 7.2; 0.15M NaCl).
3. The mixtures contained the compounds above their solubility limits, so they were vortexed, and 4.5 ml of the cloudy mixtures was spread onto microscope slides.
4. The slides remained at room temperature for 1 hour to allow the agarose to solidify.
5. The, 4 mm wells were punched into the agarose, twice per slide.
6. 20 ul of the Lipase was added to each well.
7. The slides were incubated for 24 hours at 37° C.
8. A photograph of each slide is provided in FIG. 4.
9. The diameter squared was determined for each. This allows determination of hydrolysis of compound.
   GML: 15 mm; 15 mm diameters (diameters squared=225 mm)
   SGML: 12 mm; 13 mm diameters (diameters squared=144 mm and 169 mm for an average of 156.5 mm)
   S2GML: 0 mm; 0 mm diameters (diameters squared=0)
10. Diameter squared is used to the determination would be a straight line with a standard curve.
Set GML at 100%
11. SGML is 70% as much as GML
12. S2GML is 0% of GML
These numbers correlated with the slightly greater killing of *Staphylococcus aureus* by SGML compared to GML and the much greater killing by S2GML.

Example 12

| Time 0 CFU/ml | | |
|---|---|---|
| *Candida auris*: 4.5E+05 | | |
| GAS 594: 2.7E+06 | | |
| *B. subtilis*: 1.1E+07 | | |
| Determined MIC/MBC at 24 hours | | |
| Microbe | Agent Tested | MIC/MBC (ug/ml) |
| *Bacillus subtilis* | GML | 50 |
| | SGML | 10 |
| | S2GML | <1.0 |
| *Streptococcus pyogenes* | GML | 1.0 |
| | SGML | 0.1 |
| | S2GML | <0.1 |
| *Candida auris* | GML | 50 |
| | SGML | 10 |
| | S2GML | 1.0 |

*Candida auris* is a newly emerging yeast (fungus) that is causing skin and bloodstream infections in humans. It easily becomes resistant to anti-fungal agents, making development of novel therapeutics a necessity. This organism is related to *Candida albicans* and other *Candida* species. The MIC and MBC in the above table show very good activity of both the SGML and S2GML versus this organism.

*Bacillus subtilis*, an aerobic spore-former, was incubated with 200 RPM shaking at 37° C. The strain was a recent clinical isolate at the University of Iowa, and proves to develop resistance to standard anti-fungal agents.

*Streptococcus pyogenes* (Group A *Streptococcus*) 594 is a standard scarlet fever strain that has been extensively published on. The strain was incubated stationary at 37° C. in 5% $CO_2$.

All solutions used in the MBC and MIC studies were prepared from a stock of 100 mg/ml of either GML, SGML or S2GML in absolute ethanol.

INCORPORATION BY REFERENCE

All of the U.S. patents, U.S. patent application publications and non-patent publications cited herein are hereby incorporated by reference.

EQUIVALENTS

Those skilled in the art will recognize or be able to ascertain using no more than routine experimentation, many equivalents to the various embodiments of the disclosure described herein. Such equivalents are encompassed by the following claims.

We claim:
1. A compound of Formula (I),

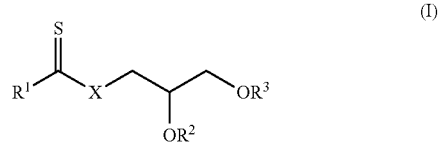

wherein:
R¹ is selected from the group consisting of alkyl, alkenyl, and alkynyl;
R² and R³ are independently selected from the group consisting of hydrogen, COR⁴, —CON(H)R⁴, —CO₂R⁴, or P(O)(OR⁴)₂; or, taken together with the carbon to which they are attached, R² and R³ may form a 3- to 5-membered aliphatic carbocyclic ring;
R⁴ is H, alkyl, alkenyl, aryl, cycloalkyl, heterocyclyl, or heteroaryl; and
X is S;
or a pharmaceutically acceptable salt thereof.
2. The compound of claim 1, wherein R¹ is an unsubstituted ($C_8$-$C_{20}$)alkyl.
3. The compound of claim 1, wherein R¹ is a substituted ($C_8$-$C_{20}$)alkyl.
4. The compound of claim 1, wherein R¹ is an unsubstituted ($C_{10}$-$C_{16}$)alkyl.
5. The compound of claim 1, wherein R¹ is a substituted ($C_{10}$-$C_{16}$)alkyl.

6. The compound of claim 1, wherein $R^1$ is an unsubstituted $C_{11}$ alkyl.

7. The compound of claim 1, wherein $R^1$ is a substituted $C_{11}$ alkyl.

8. The compound of claim 1, wherein $R^2$ is hydrogen.

9. The compound of claim 1, wherein $R^3$ is hydrogen.

10. The compound of claim 1, wherein $R^2$ is $(C_1-C_4)$alkyl.

11. The compound of claim 1, wherein $R_3$ is $(C_1-C_4)$alkyl.

12. The compound of claim 1, wherein $R^2$ or $R^3$ is —COR$^4$, —CON(H)R$^4$, —CO$_2$R$^4$, or P(O)(OH)$_2$, and $R^4$ is alkyl.

13. The compound of claim 1, wherein $R^2$ and $R^3$ are the same.

14. The compound of claim 1, wherein $R^2$ and $R^3$ are different.

15. The compound of claim 1, wherein the compound is

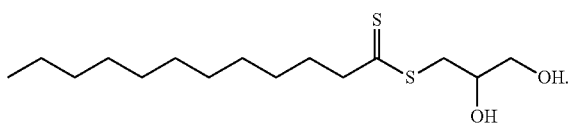 [SMILES: CCCCCCCCCCCC(=S)SCC(O)CO]

16. The compound of claim 1, wherein the compound is

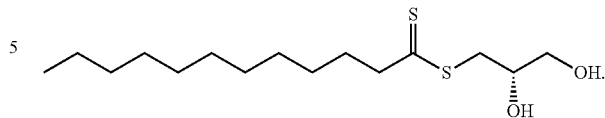

17. The compound of claim 1, wherein the compound is

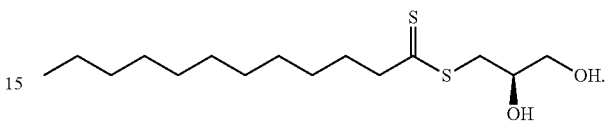

18. A pharmaceutical composition comprising a compound of claim 1 or salt thereof, and a pharmaceutical acceptable carrier.

19. A method of treating an infection comprising administering to a subject in need thereof a compound of claim 1.

20. The method of claim 19, wherein the infection is a viral infection, a bacterial infection, a fungal infection or a UTI.

* * * * *